(12) United States Patent
Leukanech

(10) Patent No.: US 6,241,700 B1
(45) Date of Patent: *Jun. 5, 2001

(54) SURGICAL HANDPIECE

(75) Inventor: Kurt D. Leukanech, Aliso Viejo, CA (US)

(73) Assignee: Alcon Laboratories, Inc., Fort Worth, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/264,593

(22) Filed: Mar. 8, 1999

(51) Int. Cl.[7] ........................................................ A61N 1/30
(52) U.S. Cl. ................................................ 604/19; 604/22
(58) Field of Search ........................... 604/22, 27, 30–35, 604/43, 39, 153; 606/107; 128/DIG. 10, DIG. 12; 601/154, 155, 160; 417/322, 323, 412, 413.1, 413.2, 413.3

(56) References Cited

U.S. PATENT DOCUMENTS

| | | | | |
|---|---|---|---|---|
| 3,920,014 | * | 11/1975 | Banico | 604/31 |
| 4,609,368 | * | 9/1986 | Datson, Jr. | 604/22 |
| 5,188,102 | * | 2/1993 | Idemoto et al. | 604/22 |
| 5,312,329 | * | 5/1994 | Besty et al. | 604/22 |
| 5,453,087 | * | 9/1995 | Malinowski | 604/22 |
| 5,462,522 | * | 10/1995 | Sakurai et al. | 604/22 |
| 5,470,305 | * | 11/1995 | Arnett et al. | 604/153 |
| 5,486,162 | * | 1/1996 | Brumbach | 604/22 |
| 5,705,018 | * | 1/1998 | Hartley | 156/345 |
| 5,733,256 | * | 3/1998 | Costin | 604/31 |
| 5,989,275 | * | 11/1999 | Estabrook et al. | 604/22 |

* cited by examiner

Primary Examiner—Manuel Mendez
(74) Attorney, Agent, or Firm—Jeffrey S. Schira

(57) ABSTRACT

A surgical handpiece having an integrated aspiration pump and vacuum and/or flow sensor. Suitable pumps included micromachined peristaltic pumps and ultrasonic pumps.

20 Claims, 4 Drawing Sheets

SURGICAL HANDPIECE

This invention relates to a surgical handpiece and more particularly an ophthalmic phacoemulsification handpiece.

BACKGROUND OF THE INVENTION

A typical ultrasonic surgical device suitable for ophthalmic procedures consists of an ultrasonically driven handpiece, an attached hollow cutting tip, an irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece at its nodal points. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve. Ultrasonic handpieces and cutting tips are more fully described in U.S. Pat. Nos. 3,589,363; 4,223,676; 4,246,902; 4,493,694; 4,515,583; 4,589,415; 4,609,368; 4,869,715; and 4,922,902, the entire contents of which are incorporated herein by reference.

When used to perform phacoemulsification, the ends of the cutting tip and irrigating sleeve are inserted into a small incision of predetermined width in the cornea, sclera, or other location in the eye tissue in order to gain access to the anterior chamber of the eye. The cutting tip is ultrasonically vibrated along its longitudinal axis within the irrigating sleeve by the crystal-driven ultrasonic horn, thereby emulsifying upon contact the selected tissue in situ. The hollow bore of the cutting tip communicates with the bore in the horn that in turn communicates with the aspiration line from the handpiece to the console. A reduced pressure or vacuum source or a flow source in the console draws or aspirates the emulsified tissue from the eye through the open end of the cutting tip, the bore of the cutting tip, the horn bore, and the aspiration line and into a collection device. The aspiration of emulsified tissue is aided by a saline flushing solution or irrigant that is injected into the surgical site through the small annular gap between the inside surface of the irrigating sleeve and the outside surface of the cutting tip.

Existing phacoemulsification systems have the aspiration pumping mechanism and the vacuum sensing hardware contained within the console. The irrigation and aspiration tubings used to connect the handpiece to the control console typically can be up to two meters in length. These flexible tubings necessarily introduce some fluidic compliance and/or delay into the otherwise closed fluid systems, making it difficult to control exactly what is occurring at the surgical site.

One suggested method of increasing the fluidic response of the system is disclosed in U.S. Pat. No. 5,733,256, the entire contents of which being incorporated herein by reference. The system disclosed in this patent places the pressure, vacuum and flow sensors either in, or very near to, the handpiece. While such an arrangement can increase the sensitivity of the system, the aspiration pumping mechanism is located in the control console, allowing the fluidic compliance and delay difficulties associated with the prior art systems to remain.

Accordingly, a need continues to exist for an integrated ultrasonic handpiece that minimizes fluidic compliance and delay.

BRIEF SUMMARY OF THE INVENTION

The present invention improves upon prior art surgical handpieces by integrating the aspiration pump and vacuum and/or flow sensors within the handpiece. Suitable pumps include micromachined peristaltic pumps and ultrasonic pumps.

Accordingly, one objective of the present invention to provide a phacoemulsification system that minimizes fluidic compliance and delay.

A further objective of the present invention to provide an ultrasonic handpiece having an integrated vacuum and/or flow sensors.

Another objective of the present invention to provide an ultrasonic handpiece having an integrated aspiration pump.

Other objects, features and advantages of the present invention will become apparent with reference to the drawings, and the following description of the drawings and claims.

DETAILED DESCRIPTION OF THE INVENTION

Figure 1:
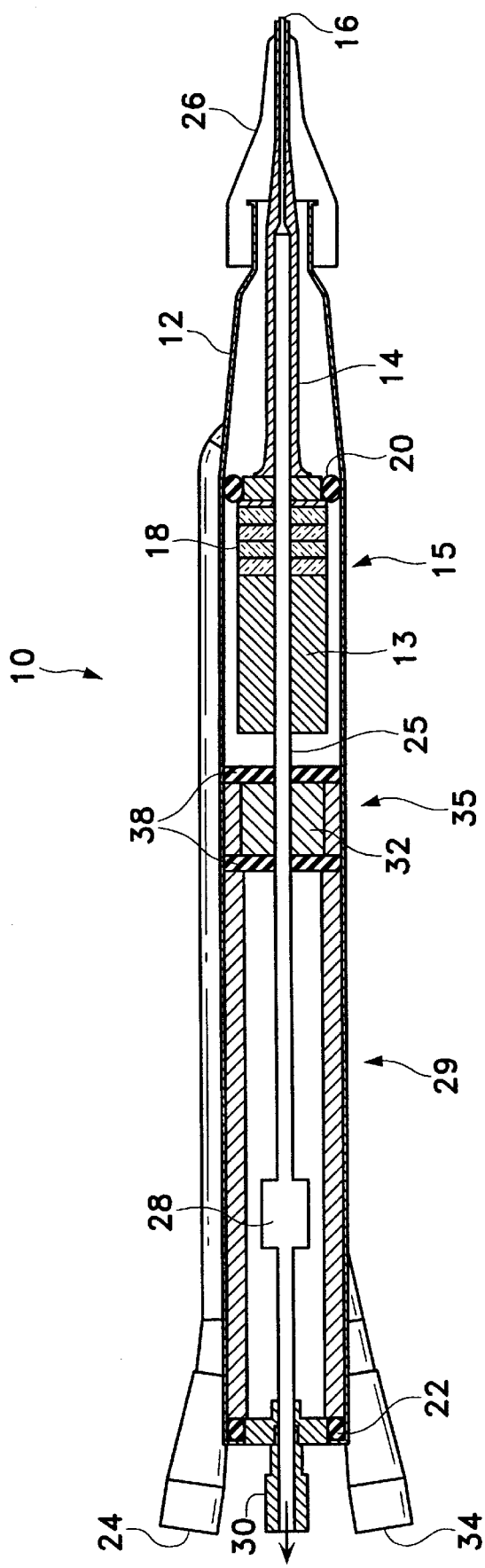
FIG. 1 is a schematic cross-sectional view of the handpiece of the present invention.

As best seen in FIG. 1, handpiece 10 of the present invention is generally divided into proximal pumping section 29, medial sensing section 35 and distal transducer section 15, which are contained within hollow outer shell 12. Distal transducer section 15 includes ultrasonic horn 14, ultrasonic cutting tip 16, compression nut 13 and piezoelectric crystals 18. Distal transducer section 15 is held within hollow shell 12 by seals 20 and 22. Shell 12 and distal transducer section 15 are of any conventional construction well-known in the art.

Proximal pumping section 29 generally contains pump 28 which aspirates fluid from the surgical site through tip 16, lumen 25 and out aspiration port 30. Pump 28 may be any suitable micropump, such as the ultrasonic micropump described below, or a micromachined peristaltic pump such as the pump described in U.S. Pat. No. 5,705,018, the entire contents of which being incorporated herein by reference.

Medial sensing section 35 generally contains sensor 32, which may be any suitable vacuum or flow sensor such as the MEMS sensor described in U.S. Pat. No. 5,733,256 or sensor Model No. EPI-050 available from Entran Devices. Sensor 32 provides feedback to the control console (not shown) for precise monitoring and control of vacuum and/or flow in handpiece 10. Isolator 38 helps prevent mechanical energy transfer between pumping section 29 and transducer section 15. Suitable isolators 38 include silicone rubber O-rings.

Pumping section 29, sensing section 35 and transducer section 15 are held within hollow shell 12 by seals 20 and 22. Seals 20 and 22 may be of any conventional construction well-known in the art.

Irrigation fluid is supplied to the surgical site through lumen 24 and tip cap sleeve 26 in a conventional manner. Electric power and feedback signals for pump 28, sensor 32 and piezoelectric crystals 18 are provided to/from the control console (not shown) through electrical fitting 34.

Figure 4:
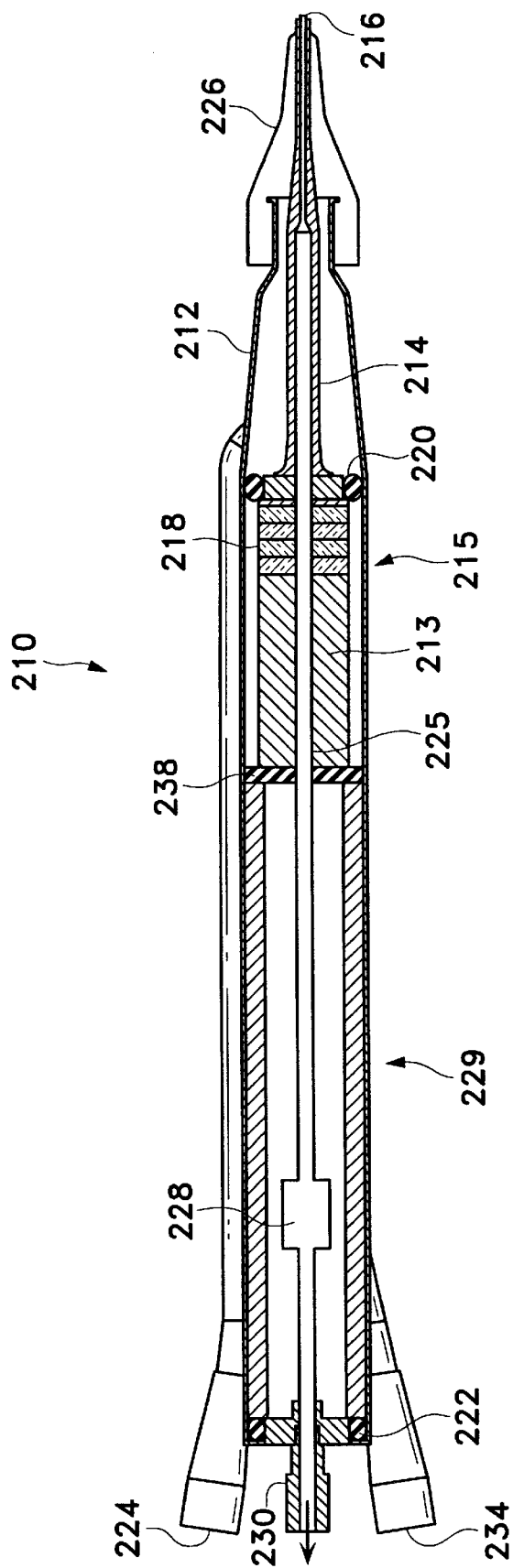
FIG. 4 is a cross-sectional view of a second embodiment of the handpiece of the present invention similar to FIG. 1 but without a medial sensing section.

As best seen in FIG. 4, handpiece 210 may alternatively be constructed without medial sensor section 35.

Figure 2:
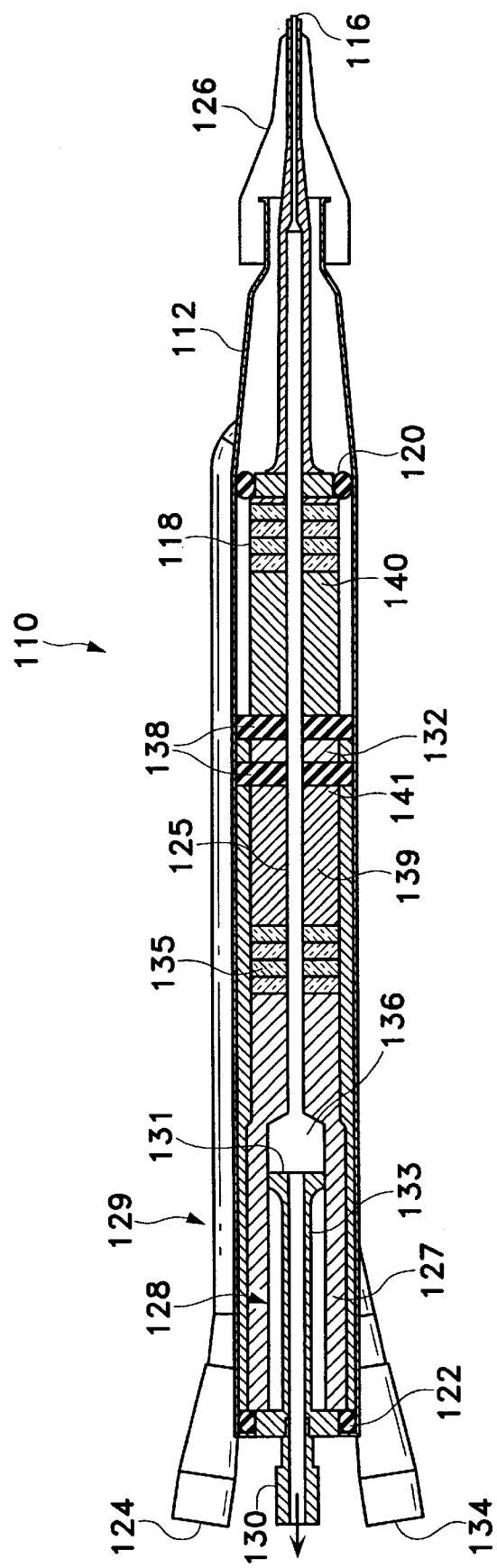
FIG. 2 is a cross-sectional view of one embodiment of the handpiece of the present invention.

As best seen in FIG. 2, proximal pumping section 129 of handpiece 110 may contain ultrasonic micropump 128, having external ultrasonic pump horn 127 and internal ultrasonic pump horn 133, piezoelectric crystals 135 and compression nut 139. Pumping chamber 136 is formed between internal horn 133 and external horn 127. Internal horn 133 may be threaded at rear seal 122 to allow internal horn 133 to be replaced. This internal horn design places a nodal point at rear seal 122 and allows aspiration port 130 to be connected directly to this nodal point. The pumping action within micropump 128 is created by the pressure differential produced by pump horn 133 and the fluid within pumping chamber 136. Micropump 128, at resonant frequency, produces vibrational nodes at crystals 135 and rear seal 122 and vibrational antinodes at distal end 131 of pump horn 133 and distal end 141 of compression nut 139.

Figure 3:
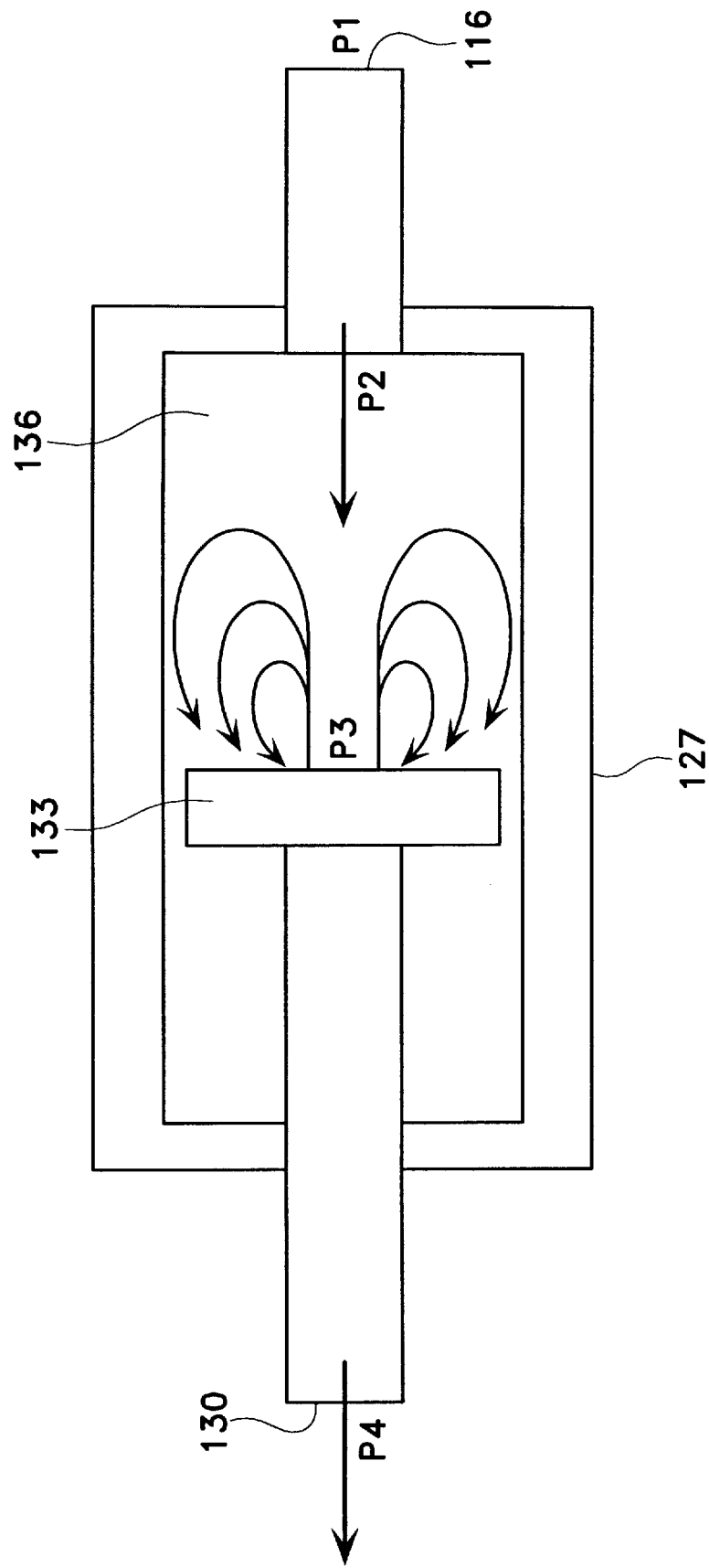
FIG. 3 is a schematic illustration of the operation of an ultrasonic pump that may be used with the present invention.

FIG. 3 generally illustrates the operation of micropump 128. As internal pump horn 133 vibrates, there is a net increase in pressure at point P3 relative to point P2 that is created by the nonlinearities in energy transfer between internal pump horn 133 and the fluid within pumping chamber 136. Using the feedback signal from sensor 132, the control console (not shown) can precisely control the vacuum and/or flow within lumen 125 by adjusting the power supplied to piezoelectric crystals 135. Placing both the sensor and the pump immediate to the surgical site minimizes the control delay of conventional systems.

While certain embodiments of the present invention have been described above, these descriptions are given for purposes of illustration and explanation. Variations, changes, modifications and departures from the systems and methods disclosed above may be adopted without departure from the scope or spirit of the present invention.

I claim:

1. A surgical handpiece, comprising:
   a) an outer shell;
   b) a pumping section having a micropump, the pumping section held within the outer shell by seals so as to allow the micropump to aspirate fluid from a surgical site; and
   c) an ultrasonic transducer section held within the outer shell by seals.

2. The device of claim 1, further comprising a sensor section held within the outer shell and separated from the pumping section and the transducer section by an isolator.

3. The device of claim 1, wherein the micropump is a micromachined peristaltic pump.

4. The device of claim 1, wherein the micropump is an ultrasonic pump.

5. The device of claim 2, wherein the micropump is a micromachined peristaltic pump.

6. The device of claim 2, wherein the micropump is an ultrasonic pump.

7. The device of claim 2, wherein the sensor section contains a flow sensor.

8. The device of claim 2, wherein the sensor section contains a vacuum sensor.

9. The device of claim 7, wherein the micropump is an ultrasonic pump.

10. The device of claim 7, wherein the micropump is a micromachined peristaltic pump.

11. The device of claim 8, wherein the micropump is an ultrasonic pump.

12. The device of claim 8, wherein the micropump is a micromachined peristaltic pump.

13. The device of claim 1, wherein the micropump is an ultrasonic pump having an external pump horn and a removable internal pump horn.

14. The device of claim 13, wherein the removable internal pump horn is held within the external pump horn by a rear seal, and a nodal point of the internal pump horn is located at the rear seal.

15. A surgical handpiece, comprising:
   a) an outer shell;
   b) a pumping section held within the outer shell by seals and having a ultrasonic pump, the ultrasonic pump having a pumping chamber formed between an external pump horn and an internal pump horn, wherein vibration of the internal pump horn creates a pumping action.

16. The device of claim 15, wherein an aspiration port is located at a nodal point on the internal pump horn.

17. A surgical handpiece, comprising:
   a) an outer shell; and
   b) a pumping section having a peristaltic micropump, the pumping section held within the outer shell by seals so as allow the micropump to aspirate fluid from a surgical site, wherein the peristaltic pump is formed by a channel covered by a membrane.

18. The device of claim 17, further comprising a sensor section held within the outer shell and proximal to the micropump.

19. The device of claim 18, wherein the sensor section contains a flow sensor.

20. The device of claim 18, wherein the sensor section contains a vacuum sensor.

* * * * *